(12) United States Patent
Jang et al.

(10) Patent No.: US 11,168,109 B2
(45) Date of Patent: Nov. 9, 2021

(54) PROCESS FOR PREPARATION OF PHYSIOLOGICALLY ACTIVE POLYPEPTIDE COMPLEX

(71) Applicant: HANMI SCIENCE CO., LTD, Hwaseong-si (KR)

(72) Inventors: Myung Hyun Jang, Seoul (KR); Min Young Kim, Suwon-si (KR); Jong-soo Lee, Seongnam-si (KR); Dae Jin Kim, Hwaseong-si (KR); Sung Min Bae, Sengnam-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 14/383,334

(22) PCT Filed: Mar. 8, 2013

(86) PCT No.: PCT/KR2013/001885
§ 371 (c)(1),
(2) Date: Sep. 5, 2014

(87) PCT Pub. No.: WO2013/133659
PCT Pub. Date: Sep. 12, 2013

(65) Prior Publication Data
US 2015/0299247 A1    Oct. 22, 2015

(30) Foreign Application Priority Data

Mar. 8, 2012  (KR) ........................ 10-2012-0024136

(51) Int. Cl.
C07K 1/107 (2006.01)
A61K 47/60 (2017.01)
A61K 47/68 (2017.01)
A61K 38/28 (2006.01)

(52) U.S. Cl.
CPC ............ *C07K 1/1077* (2013.01); *A61K 38/28* (2013.01); *A61K 47/60* (2017.08); *A61K 47/68* (2017.08); *A61K 47/6883* (2017.08); *C07K 1/1075* (2013.01); *C07K 2319/30* (2013.01)

(58) Field of Classification Search
CPC ........ A61K 47/48215; A61K 47/48369; A61K 2300/00; A61K 38/26; A61K 47/48692; A61K 38/28; A61K 47/48423; A61K 47/48507; A61K 47/48715; A61K 2039/505; A61K /; C07K 2319/30; C07K 19/00; C07K 14/62; C07K 14/505; C07K 16/00; C07K 16/46
See application file for complete search history.

(56) References Cited

U.S. PATENT DOCUMENTS

| | | | |
|---|---|---|---|
| 6,756,480 B2 | 6/2004 | Kostenuik et al. | |
| 6,924,264 B1 | 8/2005 | Prickett et al. | |
| 7,256,258 B2 | 8/2007 | Piquet et al. | |
| 7,737,260 B2 * | 6/2010 | Kim ................. | A61K 47/48415 530/391.9 |
| 8,163,889 B2 * | 4/2012 | Kim ................. | A61K 47/48215 530/391.9 |
| 8,263,084 B2 | 9/2012 | Song et al. | |
| 8,476,230 B2 | 7/2013 | Song et al. | |
| 8,829,163 B2 | 9/2014 | Bae et al. | |
| 8,895,281 B2 | 11/2014 | Song et al. | |
| 9,061,072 B2 | 6/2015 | Hong et al. | |
| 9,072,794 B2 * | 7/2015 | Woo ................... | A61K 31/4164 |
| 9,186,415 B2 | 11/2015 | Kim et al. | |
| 9,421,244 B2 | 8/2016 | Kim et al. | |
| 9,492,507 B2 | 11/2016 | Song et al. | |
| 9,504,757 B2 | 11/2016 | Kim et al. | |
| 9,597,378 B2 | 3/2017 | Kim et al. | |
| 9,636,420 B2 * | 5/2017 | Song ..................... | C07K 14/59 |
| 9,669,105 B2 | 6/2017 | Im et al. | |
| 9,724,420 B2 | 8/2017 | Kim et al. | |

(Continued)

FOREIGN PATENT DOCUMENTS

| | | |
|---|---|---|
| CN | 1777440 A | 5/2006 |
| CN | 102112493 A | 6/2011 |

(Continued)

OTHER PUBLICATIONS

European Patent Office; Communication dated Nov. 12, 2015 in counterpart application No. 13757904.1.
Korean Intellectual Property Office; Communication dated Dec. 4, 2015 in counterpart application No. 10-2013-0025344.
N.C. Ton et al., "Phase I Evaluation of CDP791, a PEGylated Di-Fab Conjugate that Binds Vascular Endothelial Growth Factor Receptor 2", Clin Cancer Res 2007, Dec. 1, 2007, pp. 7113-7118, vol. 13, No. 23.
Eizo Sada et al., "Resistance to Proteolysis of Antibody Ligands Modified with Polyethylene Glycol", Journal of Fermentation and Bioengineering 1991, pp. 137-139, vol. 71, No. 2.

(Continued)

*Primary Examiner* — Randall L Beane
(74) *Attorney, Agent, or Firm* — Sughrue Mion, PLLC

(57) ABSTRACT

Disclosed is a method for the preparation of a complex in which a physiologically active polypeptide is covalently bonded to an immunoglobulin constant region via a non-peptidyl linker. The method is characterized by the employment of a reducing agent, by which conventional problems of low production yield and modification of the polypeptide can be overcome. The physiologically active polypeptide-non-peptidyl polymer-immunoglobulin constant region complex can be produced with high purity and yield as well as at low cost. Thus, the method is industrially useful. Moreover, by exhibiting a prolonged action profile, the physiologically active polypeptide-non-peptidyl polymer-immunoglobulin constant region complex can be effectively used for developing long-acting formulations of physiologically active polypeptides which have improved drug compliance.

15 Claims, No Drawings

Specification includes a Sequence Listing.

(56) References Cited

U.S. PATENT DOCUMENTS

| | | |
|---|---|---|
| 9,731,031 B2 | 8/2017 | Jung et al. |
| 9,750,820 B2 | 9/2017 | Jung et al. |
| 9,789,202 B2 | 10/2017 | Jung et al. |
| 9,801,950 B2 | 10/2017 | Kim et al. |
| 9,833,516 B2 | 12/2017 | Lim et al. |
| 9,867,777 B2 | 1/2018 | Lee et al. |
| 9,901,621 B2 | 2/2018 | Jung et al. |
| 9,981,017 B2 | 5/2018 | Song et al. |
| 10,046,061 B2 * | 8/2018 | Jang ........................ A61K 38/28 |
| 10,071,171 B2 * | 9/2018 | Song ................ A61K 47/6889 |
| 10,660,940 B2 * | 5/2020 | Jang ........................ C07K 14/62 |
| 2003/0228652 A1 | 12/2003 | Radhakrishnan et al. |
| 2004/0180054 A1 | 9/2004 | Kim et al. |
| 2006/0269533 A1 | 11/2006 | Molin et al. |
| 2006/0269553 A1 * | 11/2006 | Kim ........................ C07K 14/56 424/155.1 |
| 2007/0083006 A1 * | 4/2007 | Hinds ........................ A61P 1/18 525/54.1 |
| 2009/0053246 A1 | 2/2009 | Kim et al. |
| 2009/0252703 A1 * | 10/2009 | Gegg, Jr. ................ A61K 47/60 424/85.2 |
| 2010/0105869 A1 * | 4/2010 | Kim ................ A61K 47/48215 530/351 |
| 2010/0255014 A1 * | 10/2010 | Kim ................ A61K 47/48415 424/181.1 |
| 2011/0200623 A1 * | 8/2011 | Song ................ A61K 47/48215 424/178.1 |
| 2013/0028918 A1 | 1/2013 | Song et al. |
| 2013/0288333 A1 | 10/2013 | Kim et al. |
| 2014/0005361 A1 | 1/2014 | Gillies et al. |
| 2014/0120120 A1 | 5/2014 | Woo et al. |
| 2014/0296475 A1 | 10/2014 | Kim et al. |
| 2014/0377290 A1 * | 12/2014 | Kim ........................ A61K 38/26 424/179.1 |
| 2015/0025227 A1 | 1/2015 | Jung et al. |
| 2015/0118255 A1 | 4/2015 | Lim et al. |
| 2015/0196643 A1 | 7/2015 | Lim et al. |
| 2015/0299282 A1 | 10/2015 | Kim et al. |
| 2016/0000931 A1 * | 1/2016 | Jang ........................ A61K 38/28 530/391.9 |
| 2016/0008483 A1 * | 1/2016 | Hwang ............ A61K 47/48415 530/303 |
| 2016/0008484 A1 * | 1/2016 | Jang ........................ C07K 14/62 530/391.7 |
| 2016/0051696 A1 * | 2/2016 | Song ................ A61K 47/48215 424/178.1 |
| 2016/0152684 A1 | 6/2016 | Hwang et al. |
| 2016/0158378 A1 | 6/2016 | Park et al. |
| 2016/0213789 A1 | 7/2016 | Rim et al. |
| 2017/0100488 A1 | 4/2017 | Park et al. |
| 2017/0196943 A1 | 7/2017 | Jung et al. |
| 2017/0340753 A1 | 11/2017 | Jung et al. |
| 2017/0360939 A1 | 12/2017 | Kim et al. |
| 2018/0015175 A1 | 1/2018 | Kim et al. |
| 2019/0083579 A1 | 3/2019 | Woo et al. |
| 2019/0119347 A1 | 4/2019 | Kim et al. |
| 2019/0153060 A1 | 5/2019 | Oh et al. |
| 2019/0269779 A1 | 9/2019 | Kim et al. |
| 2019/0269787 A1 | 9/2019 | Jung et al. |

FOREIGN PATENT DOCUMENTS

| | | | |
|---|---|---|---|
| CN | 103509118 A | 1/2014 | |
| EP | 0 330 227 A2 | 8/1989 | |
| EP | 1682581 A1 | 7/2006 | |
| HU | 213 019 B | 1/1997 | |
| JP | 2006-520384 A | 9/2006 | |
| JP | 2007531513 A | 11/2007 | |
| JP | 2008-538200 A | 10/2008 | |
| JP | 2008-543916 A | 12/2008 | |
| JP | 2010515677 A | 5/2010 | |
| JP | 2011-505355 A | 2/2011 | |
| JP | 2011-529046 A | 12/2011 | |
| JP | 2013-500375 A | 1/2013 | |
| JP | 2013537525 A | 10/2013 | |
| KR | 1020040081378 A | 9/2004 | |
| KR | 1020050047032 A | 5/2005 | |
| KR | 10-0775343 B1 | 11/2007 | |
| KR | 10-0824505 B1 | 4/2008 | |
| KR | 10-2008-0064750 A | 7/2008 | |
| KR | 10-2009-0056796 A | 6/2009 | |
| KR | 10-2010-0010919 A | 2/2010 | |
| KR | 1020100105494 A | 9/2010 | |
| KR | 10-2011-0134210 A | 12/2011 | |
| KR | 10-2012-0043207 A | 5/2012 | |
| KR | 10-2014-0037961 A | 3/2014 | |
| RU | 2428430 C2 | 9/2009 | |
| RU | 2519073 C1 | 6/2014 | |
| RU | 2014117563 A | 12/2015 | |
| TW | 200936154 | 9/2009 | |
| TW | 201004649 A1 | 2/2010 | |
| TW | 201204382 A1 | 2/2012 | |
| WO | 96/32478 A1 | 10/1996 | |
| WO | 97/34631 A1 | 9/1997 | |
| WO | 02/046227 A2 | 6/2002 | |
| WO | 2005/047336 A1 | 5/2005 | |
| WO | 2006/000448 A2 | 1/2006 | |
| WO | 2006/076471 A2 | 7/2006 | |
| WO | 2009/011544 A2 | 1/2009 | |
| WO | 2009020094 A1 | 2/2009 | |
| WO | 2009/069983 A2 | 6/2009 | |
| WO | 2010/011096 A2 | 1/2010 | |
| WO | 2010/080606 A1 | 7/2010 | |
| WO | 2010107256 A2 | 9/2010 | |
| WO | WO-2010107256 A2 * | 9/2010 | ........... C07K 14/575 |
| WO | 2011/011073 A1 | 1/2011 | |
| WO | 2011/064758 A2 | 6/2011 | |
| WO | 2011/122921 A2 | 10/2011 | |
| WO | 2012/011752 A2 | 1/2012 | |
| WO | 2012137479 A1 | 10/2012 | |
| WO | 2012/165915 A2 | 12/2012 | |
| WO | 2012/169798 A2 | 12/2012 | |
| WO | 2012173422 A1 | 12/2012 | |
| WO | 2013/066106 A1 | 5/2013 | |
| WO | 2013100704 A1 | 7/2013 | |
| WO | 2013/119903 A1 | 8/2013 | |
| WO | 2013133659 A1 | 9/2013 | |
| WO | 2014013262 A1 | 1/2014 | |
| WO | 2014017845 A2 | 1/2014 | |
| WO | 2014017849 A1 | 1/2014 | |
| WO | 2014/133327 A1 | 9/2014 | |
| WO | 2014/137161 A1 | 9/2014 | |

OTHER PUBLICATIONS

International Searching Authority International Search Report for PCT/KR2013/001885 dated Jun. 25, 2013.
International Searching Authority, Written Opinion for PCT/KR2013/001885 dated Jun. 25, 2013.
Korean Intellectual Property Office; Communication dated Aug. 23, 2016 in counterpart application No. 10-2013-0025344.
The State Intellectual Property Office of P.R.C., Communication dated May 17, 2016, issued in counterpart Chinese Application No. 201380023673.2.
Taiwan Patent Office; Examination Report dated Jul. 19, 2017 in counterpart Taiwanese Patent Application No. 102108193.
Russian Patent Office; Communication dated Dec. 19, 2016 in counterpart Russian application No. 2014138621/10.
RU application No. 2015139510 (44 pgs. total).
RU Application No. 2015133462 (38 pgs. total).
Japan Patent Office; Communication dated Feb. 1, 2017 in counterpart JP application No. 2014-560857.
Brazilian Patent Office, Communication dated Oct. 22, 2019, issued in application No. BR112014022187-1.
International Searching Authority International Preliminary Report on Patentability dated Sep. 9, 2014 in International Application No. PCT/KR2013/001885.
Dinesen et al., "Targeting nanomedicines in the treatment of Crohn's disease: focus on certolizumab pegol (CDP870)", International Journal of Nanomedicine, vol. 2, No. 1, pp. 39-47, 2007.

(56) References Cited

OTHER PUBLICATIONS

Ton et al., "Phase I Evaluation of CDP791, a PEGylated Di-Fab Conjugate that Binds Vascular Endothelial Growth Factor Receptor 2", Clinical Cancer Research, vol. 13, No. 23, pp. 7113-7118, 2007.
Amit Chaudhary et al. "Enhancement of solubilization and bioavailability of poorly soluble drugs by physical and chemical modifications: A recent review", Journal of Advanced Pharmacy Education & Research, 2012, pp. 32-67, vol. 2, No. 1.
Bandela et al., "Advanced peglyation for the development of raloxifene hydrochloride, bcs class ii drug", J Young Pharm (2009) 1(4) p. 295-300.
Bell et al., "To fuse or not to fuse: What is your purpose?", Protein Science, 2013, vol. 22, pp. 1466-1477 (12 pages total).
Chang Ki Lim et al., "Pharmacological Benefits of Once Weekly Combination Treatment using LAPS-Insulin and LAPS-Exendin-4 in Animal Models", DIABETES, Jul. 1, 2013, vol. 62, 950-P, XP055455455, p. A242.
Chinese Intellectual Property Office, communication dated May 14, 2015 issued in Chinese application No. 201280054295.X.
Communication dated Aug. 29, 2016 by the Japanese Patent Office in Japanese Patent Application No. 2014-539876.
Communication dated Feb. 3, 2016, issued by the Korean Intellectual Property Office in Korean application No. 10-2011-0114828.
Communication dated Mar. 21, 2018 from the European Patent Office in Application No. 15772562.3.
Communication dated Nov. 2, 2017 from the European Patent Office in European application No. 15772562.3.
Communication dated Dec. 2, 2016 by the Hungarian Patent Office in Hungarian Application No. P 16 00621.
Communication dated Oct. 2, 2017 by the Hungarian Patent Office in Application No. P1600621/11.
Cunningham-Rundles, et al., "Biological activities of polyethyleneglycol immunoglobulin conjugates", Journal of Immunological Methods, vol. 152, 1992, pp. 177-190 (14 pages).
Czajkowsky et al., "Fc-fusion proteins: new developments and future perspectives", EMBO Molecular Medicine, vol. 4, pp. 1015-1028 (2012) (14 pages total).
European Patent Office, communication dated Feb. 17, 2015 issued in European application No. 12845690.2.
Flanagan, M., et al., "Soluble Fc Fusion Proteins for Biomedical Research", Methods in Molecular Biology 378, 2007, 17 pages.
International Search Report of PCT/KR2015/003195 dated Jun. 18, 2015.
Japanese Patent Office; Communication dated Nov. 22, 2018 in application No. 2016-560523.
Korean Patent Office; Communication dated Feb. 15, 2019 in application No. 10-2018-0018494.
Malaysian Patent Office; Communication dated Jun. 15, 2017, in application No. PI 2014001177.
Meier, P., et al., "Soluble Dimeric Prion Protein Binds PrPsc In Vivo and Antagonizes Prion Disease", Cell, vol. 113, No. 1, 2003, p. 49-60 (12 pages).
Mitchell, et al., "Targeting Primary Human Ph+ B-Cell Precursor Leukemia-Engrafted SCID Mice Using Radiolabeled Anti-CD19 Monoclonal Antibodies", The Journal of Nuclear Medicine, 2003, vol. 44, pp. 1105-1112 (9 pages).
Paul J Carter, "Introduction to current and future protein therapeutics: A protein engineering perspective", Experimental Cell Research, Elsevier, Feb. 2011, vol. 317, No. 9, XP028205664, pp. 1261-1269 (total 9 pages).
Russian Patent Office: Communication dated Sep. 27, 2016 in application No. 2014117563/10(027801).
State Intellectual Property Office of the P.R.C., Communication dated Nov. 12, 2015, issued in Chinese Application No. 201280054295.X.
Young Jin Park et al., "Pharmacokinetics and Pharmacodynamics of Ultra-Long Acting Insulin (LAPS-Insulin) in Animal Models", DIABETES, Jun. 1, 2012, vol. 61, 919-P, XP055455447, p. A234.
Hazra et al., Biotechnology Progress, 2010, vol. 26, No. 6, pp. 1695-1704.
International Searching Authority International Search Report for PCT/KR2012/009186 dated Mar. 28, 2013.
AAT Bioquest®, Inc., "SMCC and SMCC Plus™ Protein Crosslinkers", Product Technical Information Sheet, Jul. 2012, 3 pages total.
Yu-Ting Liu et al., "Synthesis and characterization of novel ternary deep eutectic solvents", Chinese Chemical Letters, 2014, vol. 25, Issue 01, pp. 104-106 (3 pages total)(online Oct. 2013).
PubChem entry for propylene glycol, https://pubchem.ncbi.nlm.nih.gov/compound/Propylene-glycol, retrieved Jun. 3, 2021 (75 pages).
Pasut, "Polymers for Protein Conjugation", Polymers, Jan. 13, 2014, vol. 6, pp. 160-178.

\* cited by examiner

PROCESS FOR PREPARATION OF PHYSIOLOGICALLY ACTIVE POLYPEPTIDE COMPLEX

CROSS REFERENCE TO RELATED APPLICATIONS

This application is a National Stage of International Application No. PCT/KR2013/001885 filed Mar. 8, 2013, claiming priority based on Korean Patent Application No. 10-2012-0024136 filed Mar. 8, 2012, the contents of all of which are incorporated herein by reference in their entirety.

TECHNICAL FIELD

The present invention relates to a method for the preparation of a complex in which a physiologically active polypeptide is covalently bonded to an immunoglobulin constant region via a non-peptidyl polymer linker comprising two or more aldehydes as functional groups. More particularly, the present invention relates to a method for effectively preparing a physiologically active polypeptide complex, characterized by improving problems of low production yield and reagent polypeptide deformation by adjusting the usage of a reducing agent when preparing the same.

BACKGROUND ART

On the whole, physiologically active polypeptides are easy to denature due to their low stability, and readily undergo proteolytic degradation in blood and subsequent renal or hepatic clearance. Hence, protein drugs containing physiologically active polypeptides as pharmaceutical ingredients need to be frequently administered to patients in order to maintain appropriate serum levels and titers. However, such frequent administration of protein drugs, most of which is in the form of injections, causes pain to patients and has a high cost of treatment. To solve these problems, a lot of effort has been put into improving the serum stability of protein drugs and maintaining the drugs in the blood at high levels for a prolonged period of time to maximize the pharmaceutical efficacy of the drugs. As a requirement for use as long-acting preparations, protein drugs must be formulated to have high stability and have their titer maintained at a sufficiently high level without incurring immune responses in patients.

A conventional approach to stabilizing proteins and preventing enzymatic degradation and renal clearance is to chemically modify the surface of a protein drug with a polymer having high solubility, such as polyethylene glycol (hereinafter referred to as "PEG"). By binding to specific or various regions of a target protein, PEG makes the solubility of the protein higher, thereby stabilizing the protein and preventing hydrolysis without causing serious side effects (Sada et al., J. Fermentation Bioengineering 71: 137-139).

For example, WO 2006/076471 discloses a way to make B-type natriuretic peptide (BNP) long-acting by conjugating it with PEGs which bind to the natriuretic peptide receptor A (NPR-A) to trigger the synthesis of cGMP, thereby decreasing arterial blood pressure. It is thus used in the treatment of congestive heart failure. U.S. Pat. No. 6,924,264 describes a method for improving the in vivo duration of exendin-4 by PEGylation of its lysine residue. However, in such a method, despite its capability to enhance the circulation time of the peptide drug by increasing the molecular weight of PEG, PEGylation has problems such as greatly reducing the titers of the peptide drug and decreasing yield due to the reduced reactivity of the peptide as the molecular weight of PEG increases.

WO 02/46227 discloses fusion proteins, in which GLP-1, and exendin-4 or analogs thereof are conjugated with human serum albumin or an immunoglobulin fragment (Fc) prepared by genetic recombination. U.S. Pat. No. 6,756,480 concerns a fusion protein in which parathyroid hormone (PTH) or its analog is linked to an Fc. Although these methods may be evaluated as a solution to the problems of PEGylation, such as low yield and non-specificity, their effect in increasing the in vivo half-life of the target peptides has shown to not be significant, contrary to expectation, and further in some cases the fusion proteins have low titers. While a variety of peptidyl linkers are utilized so as to maximize the effect of increasing the serum half-life, they have a potential to evoke immune responses. Further, a peptide having a disulfide bond, such as BNP, has difficulty in practical application because it is highly apt to cause misfolding. Moreover, a peptidyl linker with non-natural amino acid residue is impossible to produce through genetic recombination.

Insulin is a peptide, secreted by beta cells of the pancreas in humans, and is central to regulating blood glucose level in the body. When insulin is not secreted properly or the secreted insulin does not adequately function within the body, blood glucose levels cannot be controlled and are increased, resulting in diabetes mellitus. The latter case is called type 2 diabetes. The case where insulin cannot be secreted from the pancreas and causes increased blood glucose levels, however, results in type 1 diabetes. Patients with type 2 diabetes are treated with oral hypoglycemic agents, and some of them are treated with insulin. Meanwhile, injection of insulin is essentially required for patients with type 1 diabetes.

Typically, insulin therapy is conducted by the administration of insulin via injection three times a day after or before every meal. However, continuous administration of insulin three times a day is painful and inconvenient for patients. Many attempts have been made to solve these problems. One strategy designed to increase the permeability of protein drugs in biomembranes is to deliver them by oral or nasal inhalation. However, administration by oral or nasal inhalation is significantly low in delivery efficiency when compared to injection, and has difficulty in maintaining peptide drugs at a level necessary for in vivo activity.

As an alternative strategy, an excess amount of a drug can be subcutaneously injected and absorbed into the body in a delayed manner so as to maintain a constant blood level even with injection once a day. Some of the drugs (e.g., Lantus, Sanofi-aventis) are approved for commercial use and are currently administered to patients. Separately, a study has been conducted toward the modification of insulin with fatty acids to make the binding of insulin conjugates stronger and extend the duration through combining with albumin at the site of injection or in blood. Some of the drugs (e.g., Levemir, NovoNordisk) are approved for commercial use. However, these drugs cause pain at the site of injection and must be injected once a day, which is still a great burden to patients.

To overcome the problems encountered in the prior art, the present inventors have prepared a complex comprising a physiologically active polypeptide and an immunoglobulin constant region that are connected by using a non-peptidyl polymer as a linker, as a strategy to simultaneously increase plasma half-life and in vivo duration of a physiologically active polypeptide such as insulin. However, there is also a need for a method for preparing the complex with a high yield and with high purity because the components of the complex are very expensive. With this in mind, the present inventors have developed a method to prepare the physiologically active polypeptide complexes with reduced cost, high yield and high purity by using use of proper kinds of reducing agents at an optimal concentration in a reaction solution during the reaction for complex production, thereby completing the present invention.

DISCLOSURE OF INVENTION

Technical Problem

An object of the present invention is to provide an efficient method for preparing a complex in which a physiologically active polypeptide is covalently bonded to an immunoglobulin constant region via a non-peptidyl polymer linker comprising two or more aldehydes as functional groups, characterized by improving problems of low production yield and reagent polypeptide deformation by using proper kinds of reducing agents at the optimal concentration in a reaction solution during the reaction.

Solution to Problem

In one aspect to achieve the above object, the present invention provides a method for preparing a complex of physiologically active polypeptide-non-peptidyl polymer-immunoglobulin constant region, comprising (1) reacting a non-peptidyl polymer having two or more aldehydes as functional groups with one of a physiologically active polypeptide or an immunoglobulin constant region in the presence of a reducing agent at a concentration of 1-20 mM; and (2) reacting the reaction mixture of (1) with the other of a physiologically active polypeptide or immunoglobulin constant region in the presence of a reducing agent at a concentration of 1-100 mM.

The reaction mixture may comprise a conjugate of the non-peptidyl polymer and the physiologically active polypeptide or a conjugate of the non-peptidyl polymer and the immunoglobulin constant region, and/or the reactants that remain unreacted. Hence, the method of the present invention may further comprise separating the conjugate of the physiologically active polypeptide-non-peptidyl polymer or the conjugate of the immunoglobulin-non-peptidyl polymer from the reaction mixture after the step (1).

The term "non-peptidyl polymer," as used herein, refers to a biocompatible polymer comprised of at least two repeating units which are held together by a random covalent bond other than a peptide bond. Examples of the non-peptidyl polymer useful in the present invention include polyethylene glycols, polypropylene glycols, copolymers of ethylene glycol and propylene glycol, polyoxyethylated polyols, polyvinyl alcohols, polysaccharides, dextrans, polyvinyl ethyl ethers, biodegradable polymers such as polylactic acid (PLA) and polylactic-glycolic acid (PLGA), lipid polymers, chitins, hyaluronic acid and combinations thereof, with a preference for polyethylene glycol (PEG). The derivatives thereof that are well known in the art and derivatives which can be readily prepared using methods known in the art are also within the scope of the present invention.

As described above, the non-peptidyl polymer may have two or more aldehydes as functional groups. Thus, the non-peptidyl polymer listed above may be in a bi- or multi-functional aldehyde form in itself or contain a substituent having an aldehyde group at its two or more alcohol groups, preferably. The substituent having an aldehyde group may be alkylaldehydes such as propionaldehyde or butylaldehyde. In one preferred embodiment, the non-peptidyl polymer may be PEG with a propionaldehyde substituent at each of its termini.

The disadvantage of conventional peptidyl linkers used in fusion proteins constructed by an in-frame fusion technique is that they are readily cleaved in vivo by proteinases and thus cannot guarantee the prolongation of serum half-life by the carrier, contrary to expectation. However, in the present invention, a polymer that is resistant to protease is used, and thus the plasma half-life of the peptide can be maintained at a similar level to that of the carrier. Therefore, so long as it is resistant to in vivo proteinases, any non-peptidyl polymer may be used in the present invention, without limitation. Molecular weight of the non-peptidyl polymer ranges from 1 to 100 kDa and preferably from 1 to 20 kDa. In addition, the non-peptidyl polymer which is linked to the physiologically active polypeptide may be an individual polymer or a combination of different polymers. Moreover, the non-peptidyl polymer useful in the present invention may have functional groups at its two or three ends which can be coupled to the physiologically active polypeptide and the immunoglobulin constant region. Preferably, the functional groups may be aldehyde.

Conjugation with PEG, which is typically used to prepare long-acting formulations of protein drugs, increases the stability of the proteins, while larger molecular weights of PEG exhibit lower reactivity with the proteins and thus decrease the production yield. Since the production yield is closely correlated with production cost and industrial applicability, it is very important to increase the production yield. PEG with aldehydes as functional groups may be coupled to an amine group, which is present at an N-terminus or on a side chain of Lys residue of the physiologically active polypeptide or the immunoglobulin constant region. In this regard, the yield of PEGylation may vary depending on various factors including the molar ratio of PEG to proteins, the concentration of reaction solutions, the time of reaction, pH, temperature, etc. Chem. Biol. Drug Des. 2007; 69; 132-138 describes insulin PEGylation carried out with 5 K aldehyde mPEG at a yield of over 90% by adjusting various factors including molar ratios, reaction times, pH, etc. In US 2009/0252703A1, it is reported that the addition of an organic solvent to the reaction solution increases the yield of peptide PEGylation. WO 2010/089756A2 discloses an improvement in the PEGylation yield by reacting r-metHuG-CSF with PEG in the presence of a carbohydrate.

However, when a non-peptidyl polymer including PEG with two or more functional groups is used as a linker between two different polypeptides, two or more steps in reactions are required, thus lowering the overall yield. Particularly, a step of the second reaction (wherein the physiologically active polypeptide or immunoglobulin constant region conjugated with a non-peptidyl polymer having two or more functional groups is reacted with the immunoglobulin constant region or the physiologically active polypeptide, respectively, hereinafter referred as "coupling reaction") was observed to be conducted with a significantly lower yield, compared to a step of the first reaction in which the physiologically active polypeptide or the immunoglobulin constant region is reacted with a non-peptidyl polymer having two or more functional groups.

In the present invention, the concentration of the reducing agent in the first reaction is demonstrated to have a correlation with the yield of the second coupling reaction. Higher yields of the coupling reaction were observed with lower concentrations of a reducing agent, shorter reaction times, and lower reaction temperatures in the first reaction.

As used herein, the term "reducing agent" refers to a compound that functions to reduce the reversible imine double formed from a reaction between the aldehyde group of the non-peptidyl polymer and the amine group of the polypeptides (physiologically active polypeptide, immunoglobulin constant region), thereby forming a covalent bond and is intended to encompass all reducing agents known in the art. For the purpose of the present invention, the reducing agent may be added to a reaction solution in which the non-peptidyl polymer forms a covalent bond with the physiologically active polypeptide or the immunoglobulin constant region. So long as it is typically used in the art, any reducing agent may be employed in the present invention. Examples of the reducing agent may include, but are not limited to, sodium cyanoborohydride, borane pyridine complex, sodium borohydride, borane dimethylamine complex, borane trimethylamine complex, and sodium triacetoxyborohydride. An adequate reducing agent may be selected depending on the kinds of the physiologically active polypeptide or the immunoglobulin constant region and the reaction solvent.

The reducing agent is used for conjugation of a physiologically active polypeptide or an immunoglobulin constant region with a non-peptidyl polymer. The reaction solution may contain the reducing agent in a concentration of 1-20 mM for a reaction between the physiologically active polypeptide or the immunoglobulin constant region and the non-peptidyl polymer, and in a concentration of 1-100 mM for the coupling reaction. More preferably, the reducing agent may be used in a concentration of 1-20 mM for the conjugation between the physiologically active polypeptide or the immunoglobulin constant region, and the non-peptidyl polymer, and in a concentration of 1-40 mM for the coupling reaction.

The conjugation reaction between a physiologically active polypeptide or the immunoglobulin constant region, and a non-peptidyl polymer (the reaction of step (1)) may be conducted for 1 to 16 hrs and at a temperature of from 0 to 25° C. In addition, the coupling reaction (the reaction of step (2)) may be conducted for 1 to 48 hrs.

Preferably, the reaction of step (1) may be carried out for 1 to 16 hrs at 0 to 25° C. in the presence of a reducing agent in a concentration of 1 to 20 mM while the reaction of step (2) may be carried out for 1 to 48 hrs in the presence of a reducing agent in a concentration of 1 to 40 mM.

In one preferred embodiment, sodium cyanoborohydride was used as a reducing agent at a variety of conditions, in order to increase the production yield of a complex in which insulin, PEG linker having two or more aldehydes as functional groups, and immunoglobulin constant region are connected together. It has been found that the yield of the coupling reaction is enhanced when the first reaction, which is performed to connect the physiologically active polypeptide or the immunoglobulin constant region and the non-peptidyl polymer, is conducted for a short time at a low temperature in the presence of a low concentration of the reducing agent (Table 1).

In another preferred embodiment, the reaction was performed with various concentrations of the reducing agent borane pyridine complex, and higher yields of the second reaction, the coupling reaction, were detected after lower concentrations of the reducing agent were used in the first reaction between a physiologically active polypeptide or an immunoglobulin constant region and a non-peptidyl polymer. The case where Sodium cyanoborohydride was used as a reducing agent shows higher yields compared to the case where borane pyridine complex was used (Table 2).

Moreover, it has been confirmed that the yield of the second, coupling reaction was increased as the concentration of a reducing agent was increased.

In one preferred embodiment, the coupling reaction was carried out at various concentrations of the reducing agent sodium cyanoborohydride, and improved yields of the coupling reaction were obtained in the presence of a high concentration of the reducing agent. However, a very high concentration of the reducing agent caused the immunoglobulin constant region to undergo aberration. In order to avoid this, the coupling reaction was carried out for 13 hrs in the presence of 20 mM sodium cyanoborohydride and it was observed that its yield was maintained at a high level and the aberration of the immunoglobulin constant region was consequently minimized (Tables 3 and 4).

As used herein, the term "physiologically active polypeptide" refers a polypeptide having a certain physiological function in vivo as a general concept. It has a polypeptidyl structure in common and shows various biological activities. When the body becomes biologically abnormal as a result of a lack or an excess of a material involved in a certain function, the physiologically active polypeptide may regulate the genetic expression or physiological function, thereby correcting the abnormality. A typical example is a protein drug.

Examples of the physiologically active polypeptides that are applied in the present invention include human growth hormone, growth hormone releasing hormones, growth hormone releasing peptides, interferon, interferon receptors, colony-stimulating factors, glucagon-like peptides (GLP-1, etc.), oxyntomodulin, G protein-coupled receptors, interleukins, interleukin receptors, enzymes, interleukin-binding proteins, cytokine-binding proteins, macrophage activating factors, macrophage peptides, B-cell factors, T-cell factors, Protein A, allergy inhibitors, cell necrosis glycoproteins, immunotoxins, lymphotoxins, tumor necrosis factor, tumor suppressors, transforming growth factor, alpha-1 antitrypsin, albumin, α-lactalbumin, apolipoprotein-E, erythropoietin, glycosylated erythropoietin, angiopoeitins, hemoglobin, thrombin, thrombin receptor activating peptides, thrombomodulin, blood factor VII, VIIa, VIII, IX and XIII, plasminogen activators, fibrin-binding peptides, urokinase, streptokinase, hirudin, Protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, cell surface antigens, virus-derived vaccine antigens, monoclonal antibodies, polyclonal antibodies, and antibody fragments.

Insulin used in the embodiment of the present invention is a kind of physiologically active peptides secreted from the pancreas when blood glucose level becomes high, which functions to control blood glucose levels by causing the liver, skeletal muscles, and fat tissue to take up glucose from the blood and store it as glycogen, and by suppressing lipolysis, a metabolism for using fat as an energy source.

The physiologically active peptides include insulin agonists, precursors, derivatives, fragments, and variants. Native insulin, fast-acting insulin, and long-acting insulin are preferred.

Native insulin is a hormone secreted from the pancreas and plays a critical role in the control of blood glucose levels by promoting the cellular uptake of glucose and inhibiting lipolysis. Insulin having a function of regulating blood glucose levels is produced from a proinsulin precursor without a function of regulating blood glucose levels, through a series of the processes. The amino acid sequence is as follows:

```
Alpha Chain:
                                          (SEQ ID NO: 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta Chain:
                                          (SEQ ID NO: 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The term "insulin agonist," as used herein, refers to a substance which can bind to an in vivo insulin receptor and exhibit the same biological activity as that of insulin regardless of the structure of insulin.

The term "insulin derivative," as used herein, refers to a peptide that functions to control blood glucose levels in vivo and has an amino acid sequence which shares at least 80% homology with native insulin. There may be a chemical substitution (e.g., alpha-methylation, alpha-hydroxylation), deletion (e.g., deamination) or modification (e.g., N-methylation, glycosylation, fatty acid) at some amino acid residues.

As used herein, the term "insulin fragment" refers to a peptide having the function of controlling blood glucose levels in vivo, prepared by adding at least one amino acid to or deleting at least one amino acid from the amino or carboxyl terminus of insulin. The added amino acid may be a non-naturally occurring amino acid (e.g., D-amino acid).

As used herein, the term "insulin variant" refers to a peptide having the amino acid sequence of which is different from that of native insulin by one or more amino acid residue but having a function of controlling blood glucose levels in vivo.

In addition, the methods used respectively for the preparation of insulin agonists, fragments and variants may be employed independently or in combination. For example, the insulin peptide useful in the present invention may include a peptide, having the amino acid sequence of which is different from that of native insulin by one or more amino acid residue, with deamination at the N-terminal residue, but functioning to control blood glucose levels in vivo.

As used herein, the term "immunoglobulin constant region" refers to an immunoglobulin fragment that is devoid of the variable regions of light and heavy chains, the constant region 1 of the heavy chain ($C_{H1}$), and the constant region of the light chain ($C_L$), that is, an Fc region comprised of the constant regions 2 and 3 of the heavy chain ($C_{H2}$ and $C_{H3}$) (or inclusive of the constant region of the heavy chain ($C_{H4}$)). Optionally, the immunoglobulin Fc region may further comprise a hinge region. Also, the immunoglobulin constant region of the present invention may be an extended immunoglobulin Fc region which comprises a part of or the entirety of the constant region 1 of the heavy chain ($C_{H1}$) and/or the constant region of the light chain ($C_L$) except only for the variable regions of heavy and light chains of the immunoglobulin so long as it shows effects substantially identical or superior to those of the native immunoglobulin constant region. Further, the immunoglobulin constant region of the present invention may be lack of a significant part of the amino acid sequence which corresponds to $C_{H2}$ and/or $C_{H3}$. Consequently, the immunoglobulin constant region of the present invention may comprise (1) $C_{H1}$ domain, $C_{H2}$ domain, $C_{H3}$ domain and $C_{H4}$ domain, (2) $C_{H1}$ domain and $C_{H2}$ domain, (3) $C_{H1}$ domain and $C_{H3}$ domain, (4) $C_{H2}$ domain and $C_{H3}$ domain, (5) a combination of one or more constant domains and an immunoglobulin hinge region (or a partial hinge region), or (6) a dimer of each constant domain of the heavy chain and the constant region of the light chain.

An immunoglobulin constant region including Fc region is a biodegradable polypeptide which can be metabolized in vivo, so that it can safely be used as a drug carrier. In addition, an immunoglobulin Fc region is more advantageous in terms of production, purification and production yield of a complex than an entire immunoglobulin molecule owing to its relatively lower molecular weight. Further, since it is devoid of Fab, which exhibits high non-homogeneity due to the difference in amino acid sequence from one antibody to another, the immunoglobulin Fc alone provides the complex with significantly enhanced homogeneity, and reduces the possibility of inducing blood antigenicity.

The immunoglobulin constant region may originate from humans or animals, such as cows, goats, pigs, mice, rabbits, hamsters, rats, guinea pigs, etc., and may be preferably of human origin. In addition, the immunoglobulin constant region may be selected from Fc fragments derived from IgG, IgA, IgD, IgE, IgM, or combinations or hybrids thereof. Preferably, the constant region is derived from IgG or IgM, which are the most abundant ones in blood, and most preferably from IgG, which is known to improve the serum half life of ligand-binding proteins.

As used herein, the term "combination" means that polypeptides encoding single-chain immunoglobulin constant regions (preferably Fc regions) of the same origin are linked to a single-chain polypeptide of a different origin to form a dimer or multimer. That is, a dimer or a multimer may be prepared by combination of two or more fragments selected from the group consisting of fragments of IgG Fc, IgA Fc, IgM Fc, IgD Fc and IgE Fc.

As used herein, the term "hybrid" means that sequences encoding two or more immunoglobulin Fc fragments of different origins are present in a single-chain of immunoglobulin constant region (preferably, an Fc region). In the present invention, various hybrid forms are possible. For example, the hybrid domain can be composed of one to four domains selected from the group consisting of $C_{H1}$, $C_{H2}$, $C_{H3}$ and $C_{H4}$ of IgG Fc, IgM Fc, IgA Fc, IgE Fc and IgD Fc, and may comprise a hinge region.

IgG is divided into the IgG1, IgG2, IgG3 and IgG4 subclasses, and the present invention may include combinations or hybrids thereof. Preferred are the IgG2 and IgG4 subclasses, and most preferred is the Fc region of IgG4 rarely having effector functions such as Complement Dependent Cytotoxicity (CDC).

The immunoglobulin constant region may have the glycosylated form to the same extent as, or in a higher or lesser extent than the native form or may be the deglycosylated form. Increased or decreased glycosylation or deglycosylation of the immunoglobulin region may be achieved by typical methods, for example, by using a chemical method, an enzymatic method or a genetic engineering method using microorganisms. Herein, when deglycosylated, the complement (C1q) binding to an immunoglobulin Fc region becomes significantly decreased and antibody-dependent cytotoxicity or complement-dependent cytotoxicity is reduced or removed, thereby not inducing unnecessary immune responses in vivo. In this context, deglycosylated or aglycosylated immunoglobulin Fc regions are more consistent with the purpose of drug carriers. Accordingly, the immunoglobulin Fc region which is the most suitable as the drug carrier of the present invention is a human IgG4-derived aglycosylated Fc region. The human-derived Fc region is more preferable than a non-human derived Fc region, which may act as an antigen in the human body and cause undesirable immune responses such as the production of a new antibody against the antigen.

Further, not only the immunoglobulin constant region with the native amino acid sequence but also its amino acid sequence mutant may be included within the scope of the immunoglobulin constant region of the present invention. The term "amino acid sequence mutant," as used herein, refers to polypeptides having an amino acid sequence that is different from the wild-type as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used in the present invention. In addition, complement fixation sites, e.g., C1q fixation sites, or ADCC sites may be eliminated from the native Fc region to remove the effector function. The techniques of preparing amino acid sequence mutants of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly. Optionally, amino acids may be modified by phosphorylation, sulfation, acrylation, glycosylation, methylation, farnesylation, acetylation, and amidation.

The above-described immunoglobulin constant region derivatives exhibit the same biological activity as that of the immunoglobulin constant region of the present invention, but have improved structural stability against heat, pH and so forth. These immunoglobulin constant regions may be obtained from native type isolated from humans or animals such as cow, goats, pigs, mice, rabbits, hamsters, rats, guinea pigs, etc., or may be their recombinants or derivatives obtained from transformed animal cells or microorganisms. Native constant regions may be obtained by protease digestion of the entire gamut of immunoglobulins isolated from human or animal samples. Immunoglobulins are cleaved into Fab and Fc by papain and into pF'c and F(ab)$_2$ by pepsin, followed by size-exclusion chromatography to separate Fc or pF'c therefrom.

Preferable is a recombinant human immunoglobulin constant region obtained from a microorganism.

Advantageous Effects of Invention

As described above, a complex of physiologically active polypeptide-non-peptidyl polymer-immunoglobulin constant region can be produced at high purity and yield as well as at low cost by the method of the present invention. Thus, the method of the present invention is industrially useful. Moreover, it can be used to develop long-acting formulations of physiologically active polypeptides which have improved drug compliance.

MODE FOR THE INVENTION

A better understanding of the present invention may be obtained through the following examples which are set forth to illustrate, but are not to be construed as limiting the present invention.

Example 1

PEGylation of Insulin Using Sodium Cyanoborohydride as Reducing Agent and Purification of Mono-PEGylated Insulin Insulin powder was dissolved in 10 mM HCl, and PEGylated at the N-terminus of the beta chain with 3.4K propion-ALD2 PEG (PEG with two propionaldehyde groups, IDB, Korea). In this regard, 5 mg/ml insulin was reacted with PEG at a molar ratio of 1:2 at 4° C. to room temperature for 2 hrs. The reaction was performed in 50 mM sodium citrate buffer at pH 6.0 in 45% isopropanol in the presence of 2-20 mM sodium cyanoborohydride as a reducing agent. The reaction mixture was loaded onto an SP-HP (GE Healthcare) column, followed by eluting with a buffer containing sodium citrate (pH 3.0) and 45% EtOH, and using a concentration gradient of KCl to purify mono-PEGylated insulin.

PEGylation yields of insulin according to conditions of the reducing agent sodium cyaborohydride during the preparation of a complex comprising the insulin and the immunoglobulin Fc region are summarized in Table 1, below.

Example 2

Changes in Production Yields of a Complex of Mono-PEGylated Insulin-Immunoglobulin Fc Region According to Conditions of Sodium Cyanoborohydride as Reducing Agent Used in PEGylation To examine the production yield of the insulin-PEG-immunoglobulin Fc region complex, the mono-PEGylated insulin prepared in Example 1 was reacted with at a molar ratio of 1:1 with an immunoglobulin Fc at 25° C. for 13 hrs, with the total protein concentration set to be 20 mg/ml. This coupling reaction was carried out in 100 mM HEPES buffer containing 22 mM potassium phosphate and 10% ethanol at pH 8.2, in the presence of 20 mM sodium cyanoborohydride as a reducing agent.

The reaction mixture was loaded onto a Source 15Q (GE Healthcare) column, followed by eluting with Tris-HCl (pH 7.5) buffer and using a concentration gradient of NaCl to separate and purify unreacted insulin, unreacted immunoglobulin Fc region, an insulin-PEG-immunoglobulin Fc region complex, and an immunoglobulin Fc region coupled with two or more mono-PEGylated insulin (insulin-PEG) moieties. Production yields of the insulin-PEG-immunoglobulin Fc region complex were determined UV absorbance at 280 nm after purification by chromatography.

In Table 1, yields of the coupling reaction with an immunoglobulin Fc region are summarized according to conditions of sodium cyanoborohydride used as a reducing agent in the PEGylation of insulin.

TABLE 1

| Conc. of Sodium cyanoborohydride | RxnTime | Rxn Temp. | PEGylation yield (%) | Coupling yield (%) | Total yield (%) |
|---|---|---|---|---|---|
| 2 mM | 2 hr | 4° C. | 23.3 | 31.7 | 7.39 |
| 4 mM | 2 hr | 4° C. | 37.6 | 31 | 11.66 |
| 4 mM | 2 hr | RT | 39.2 | 28.8 | 11.29 |
| 8 mM | 2 hr | RT | 40.4 | 27.1 | 10.95 |
| 8 mM | 4 hr | 4° C. | 40.4 | 27 | 10.9 |
| 20 mM | 2 hr | 4° C. | 42.2 | 26.8 | 11.3 |

Example 3

PEGylation of Insulin Using Borane Pyridine Complex as Reducing Agent and Purification of Mono-PEGylated Insulin Insulin powder was dissolved in 10 mM HCl, and PEGylated at the N-terminus of the beta chain with 3.4K propion-ALD2 PEG (PEG with two propionaldehyde groups, IDB, Korea). In this regard, 5 mg/ml insulin was reacted with PEG at a molar ratio of 1:2 at 4° C. for 2 hrs. The reaction was performed in 50 mM sodium citrate buffer at pH 6.0 in 45% isopropanol in the presence of 3-20 mM borane pyridine complex as a reducing agent. The reaction mixture was loaded onto an SP-HP (GE Healthcare) column, followed by eluting with a buffer containing sodium citrate (pH 3.0) and 45% EtOH, and using a concentration gradient of KCl to purify mono-PEGylated insulin.

PEGylation yields of insulin according to conditions of the reducing agent borane pyridine complex during the preparation of a complex comprising the insulin and the immunoglobulin Fc region are summarized in Table 2, below.

Example 4

Changes in Production Yields of a Complex of Mono-PEGylated Insulin-Immunoglobulin Fc Region According to Conditions of Borane Pyridine Complex as Reducing Agent Used in PEGylation To examine the production yield of the insulin-PEG-immunoglobulin Fc region complex, the mono-PEGylated insulin prepared in Example 3 was reacted with at a molar ratio of 1:1 with an immunoglobulin Fc at 25° C. for 13 hrs, with the total protein concentration set to be 20 mg/ml. This coupling reaction was carried out in 100 mM HEPES buffer containing 22 mM potassium phosphate and 10% ethanol at pH 8.2, in the presence of 20 mM sodium cyanoborohydride as a reducing agent.

The reaction mixture was loaded onto a Source 15Q (GE Healthcare) column, followed by eluting with Tris-HCl (pH 7.5) buffer and using a concentration gradient of NaCl to separate and purify unreacted insulin, unreacted immunoglobulin Fc region, an insulin-PEG-immunoglobulin Fc region complex, and an immunoglobulin Fc region coupled with two or more mono-PEGylated insulin (insulin-PEG) moieties. Production yields of the insulin-PEG-immunoglobulin Fc region complex were determined UV absorbance at 280 nm after purification by chromatography.

In Table 2, yields of the coupling reaction with an immunoglobulin Fc region are summarized according to conditions of borane pyridine complex used as a reducing agent in the PEGylation of insulin.

TABLE 2

| Conc. of Borane pyridine complex | PEGylation yield (%) | Coupling yield (%) | Total yield (%) |
|---|---|---|---|
| 3 mM | 25.4 | 35.1 | 8.92 |
| 10 mM | 47.6 | 34.8 | 16.6 |
| 20 mM | 50.8 | 34.2 | 17.4 |

Example 5

Yields of Coupling Reaction and Formation of Immunoglobulin Fc Aberrant According to Concentration of Sodium Cyanoborohydride and Reaction Time To examine the formation of immunoglobulin Fc aberrant according to the concentrations of the reducing agent, and reaction times in the coupling reaction, the mono-PEGylated insulin was reacted at a molar ratio of 1:1 with an immunoglobulin Fc at 25° C. for 13-43 hrs, with the total protein concentration set to be 20 mg/ml. This coupling reaction was carried out in 100 mM HEPES buffer containing 22 mM potassium phosphate and 10% ethanol, pH 8.2, in the presence of 5-40 mM sodium cyanoborohydride.

The reaction mixture was loaded onto a Source 15Q (GE Healthcare) column, followed by eluting with Tris-HCl (pH 7.5) buffer and using a concentration gradient of NaCl to separate and purify unreacted insulin, unreacted immunoglobulin Fc region, an insulin-PEG-immunoglobulin Fc region complex, and an immunoglobulin Fc region coupled with two or more mono-PEGylated insulin (insulin-PEG) moieties. Production yields of the insulin-PEG-immunoglobulin Fc region complex were determined UV absorbance at 280 nm after purification by chromatography.

In Table 3, yields of the coupling reaction to prepare a complex comprising the insulin and the immunoglobulin Fc region are summarized according to concentrations of sodium cyanoborohydride used as a reducing agent, and reaction times in the coupling reaction.

TABLE 3

| Rxn Time | 5 mM SCB | 20 mM SCB | 40 mM SCB |
|---|---|---|---|
| 13 hrs | 35.2% | 37.5% | 37.5% |
| 18 hrs | 36.1% | 37.7% | 37.7% |
| 37 hrs | 36.7% | 37.3% | 37.5% |
| 43 hrs | 36.8% | 37.2% | 36.8% |

The formation of immunoglobulin Fc aberrants according to the concentrations of the reducing agent in the coupling reaction was monitored by LC on a Propac SAX-10 (DIONEX) column eluting with Tris-HCl (pH 8.0) buffer and using a concentration gradient of NaCl.

In Table 4, production yields of immunoglobulin Fc aberrants are given according to concentrations of sodium cyanoborohydride and reaction times in the coupling reaction to prepare a complex comprising the insulin and the immunoglobulin Fc region.

TABLE 4

| Rxn Time | 5 mM SCB | 20 mM SCB | 40 mM SCB |
|---|---|---|---|
| 13 hrs | 4.6% | 7.0% | 7.8% |
| 18 hrs | 6.2% | 9.0% | 9.8% |
| 37 hrs | 11.7% | 14.5% | 15.3% |
| 43 hrs | 12.7% | 15.5% | 16.8% |

Example 6

PEGylation of Immunoglobulin Fc Using Sodium Cyanoborohydride as Reducing Agent and Purification of Mono-PEGylated Immunoglobulin Fc The N-terminus of immunoglobulin Fc was PEGylated with 5K propion-ALD2 PEG (PEG with three propionaldehyde groups, NOF, Japan). In this regard, 10 mg/ml immunoglobulin Fc was reacted with PEG at a molar ratio of 1:2 at 4° C. to room temperature for 4.5 hrs. The reaction was performed in 100 mM potassium phosphate buffer at pH 6.0 in the presence of 20 mM sodium cyanoborohydride as a reducing agent. The reaction mixture was loaded onto a Source 15Q column, followed by eluting with Tris-HCl (pH 7.5) buffer and using a concentration gradient of NaCl to purify mono-PEGylated immunoglobulin Fc.

Example 7

Preparation of a Complex of Mono-PEGylated Immunoglobulin Fc Region-Insulin Using Sodium Cyanoborohydride as Reducing Agent To prepare an insulin-PEG-immunoglobulin Fc region complex, the mono-PEGylated immunoglobulin Fc prepared in Example 6 was reacted with at a molar ratio of 1:4 with an insulin at 4° C. for 13 hrs, with the total protein concentration set to be 20 mg/ml. This coupling reaction was carried out in 100 mM potassium phosphate buffer at pH 6.0 in the presence of 20 mM sodium cyanoborohydride as a reducing agent.

The reaction mixture was loaded onto a Source 15Q (GE Healthcare) column for the primary purification. And the secondary purification was additionally performed with a Source 15ISO (GE Healthcare) column to obtain an insulin-PEG-immunoglobulin Fc region complex.

The invention claimed is:

1. A method for preparing a complex of insulin - polyethylene glycol-immunoglobulin Fc region, comprising:
   (1) reacting a polyethylene glycol having two aldehydes as functional groups with an insulin in the presence of a reducing agent at a concentration of from 2 to 20 mM and an alcohol; and
   (2) reacting the reaction mixture of step (1) with an immunoglobulin Fc region in the presence of a reducing agent at a concentration of 5 to 40 mM and an alcohol,
   wherein the reaction in step (1) is carried out for 1 to 16 hrs at a temperature of 4° C. to room temperature at pH 6.0, the reaction in step (2) is carried out for 13 to 43 hrs at a pH of 8.2,
   wherein the reducing agent in step (1) and the reducing agent in step (2) are sodium cyanoborohydride (SCB), and
   wherein the alcohol in step (1) is 45% (v/v) isopropanol and the alcohol in step (2) is 10% (v/v) ethanol.

2. The method of claim 1, further comprising separating a conjugate of the insulin-polyethylene glycol from the reaction mixture after step (1).

3. The method of claim 1, wherein the reducing agents used in steps (1) and (2) function to reduce a reversible imine double bond produced from bonding between the aldehyde group of the polyethylene glycol and an amine group of the insulin or the immunoglobulin Fc region to form a covalent bond.

4. The method of claim 1, wherein the polyethylene glycol is covalently bonded to each of the insulin and the immunoglobulin Fc region through the two aldehyde functional groups thereof.

5. The method of claim 1, wherein the functional groups of the polyethylene glycol are bonded to each of an amine group of the insulin and the immunoglobulin Fc region, wherein the amine group is present at an N-terminus or on a side chain of Lys residue.

6. The method of claim 1, wherein molecular weight of the polyethylene glycol ranges from 1 to 100 kDa.

7. The method of claim 1, wherein the immunoglobulin Fc region is aglycosylated.

8. The method of claim 1, wherein the immunoglobulin Fc region consists of one to four domains selected from the group consisting of $C_{H1}$, $C_{H2}$, $C_{H3}$ and $C_{H4}$ domains.

9. The method of claim 1, wherein the immunoglobulin Fc region further comprises a hinge region.

10. The method of claim 1, wherein the immunoglobulin Fc region is selected from the group consisting of constant regions derived from IgG, IgA, IgD, IgE, IgM, or combinations or hybrids thereof.

11. The method of claim 1, wherein the immunoglobulin Fc region is selected from the group consisting of constant regions of IgG1, IgG2, IgG3, IgG4, a combination thereof, and a hybrid thereof.

12. The method of claim 1, wherein the immunoglobulin Fc region is an IgG4 Fc region.

13. The method of claim 12, wherein the immunoglobulin Fc region is an aglycosylated human IgG4 Fc region.

14. The method of claim 1, wherein the step (2) is carried out in the presence of the reducing agent at a concentration of 20 mM.

15. A method for preparing a complex of insulin-polyethylene glycol-immunoglobulin Fc region, comprising:
   (1) reacting a polyethylene glycol having two aldehydes as functional groups with an insulin in the presence of a reducing agent at a concentration of from 2 to 20 mM and an alcohol;
   (2) isolating a complex of the polyethylene glycol and the insulin from reaction mixture of (1);
   (3) reacting the isolated complex of step (2) with the immunoglobulin Fc region in the presence of a reducing agent at a concentration of 5 to 40 mM and an alcohol, wherein the reducing agent in step (1) and the reducing agent in step (3) are sodium cyanoborohydride (SCB);
   wherein the step (1) is carried out for 1 to 16 hrs at a temperature of 4° C. to room temperature at a pH of 6.0, and the reaction in step (3) is carried out at a pH of 8.2 for 13-43 hrs at a temperature of 25° C., and
   wherein the alcohol in step (1) is 45% (v/v) isopropanol and the alcohol in step (3) is 10% (v/v) ethanol.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30